United States Patent [19]

Macias et al.

[11] 4,013,888
[45] Mar. 22, 1977

[54] MONITOR FOR ATMOSPHERIC POLLUTANTS

[76] Inventors: Edward S. Macias, 6907 Waterman Ave.; Rudolph B. Husar, 7162 Pershing Ave., both of University City, Mo. 63130

[22] Filed: July 24, 1975

[21] Appl. No.: 598,568

[52] U.S. Cl. .............................. 250/304; 250/364; 250/380
[51] Int. Cl.$^2$ .................................... G01T 7/02
[58] Field of Search .......... 250/304, 364, 380, 383, 250/393

[56] References Cited

UNITED STATES PATENTS

| | | | |
|---|---|---|---|
| 3,508,047 | 4/1970 | Mott et al. ................... | 250/380 X |
| 3,646,345 | 2/1972 | Plakas et al. ................. | 250/364 X |
| 3,679,898 | 7/1972 | Compton et al. ............... | 250/304 |

Primary Examiner—Archie R. Borchelt
Attorney, Agent, or Firm—Koenig, Senniger, Powers and Leavitt

[57] ABSTRACT

Apparatus for monitoring the mass concentration of atmospheric pollutants above and below a predetermined size. A receptacle has an air inlet and outlet. Air is continuously drawn through the inlet and thence through the receptacle and the outlet. A first collector in the receptacle collects pollutants above the predetermined size. This first collector is movable through a first station and collects pollutants above the predetermined size from the air entering the receptacle through the inlet on successive areas thereof. A second collector in the receptacle collects pollutants below the predetermined size. This second collector is movable through a second station and collects pollutants below the predetermined size from the air which has passed the first station on successive areas thereof. A holder is provided for a first source of radiation which passes through the area of the first collector at the first station. A detector detects radiation from the first source passing through the area of the first collector. A holder is provided for a second source of radiation which passes through the area of the second collector at the second station. A detector detects radiation from the second source passing through the area of the second collector. Periodically operating the collectors, moves the pollutant-bearing areas thereof away from the stations and brings fresh areas for collection of pollutants into position at the stations. The collectors dwell between successive operations thereof. Instrumentation responsive to the first and second detectors indicates the mass concentration of pollutants above and below the predetermined size for each dwell period between the successive operations of the collectors.

15 Claims, 2 Drawing Figures

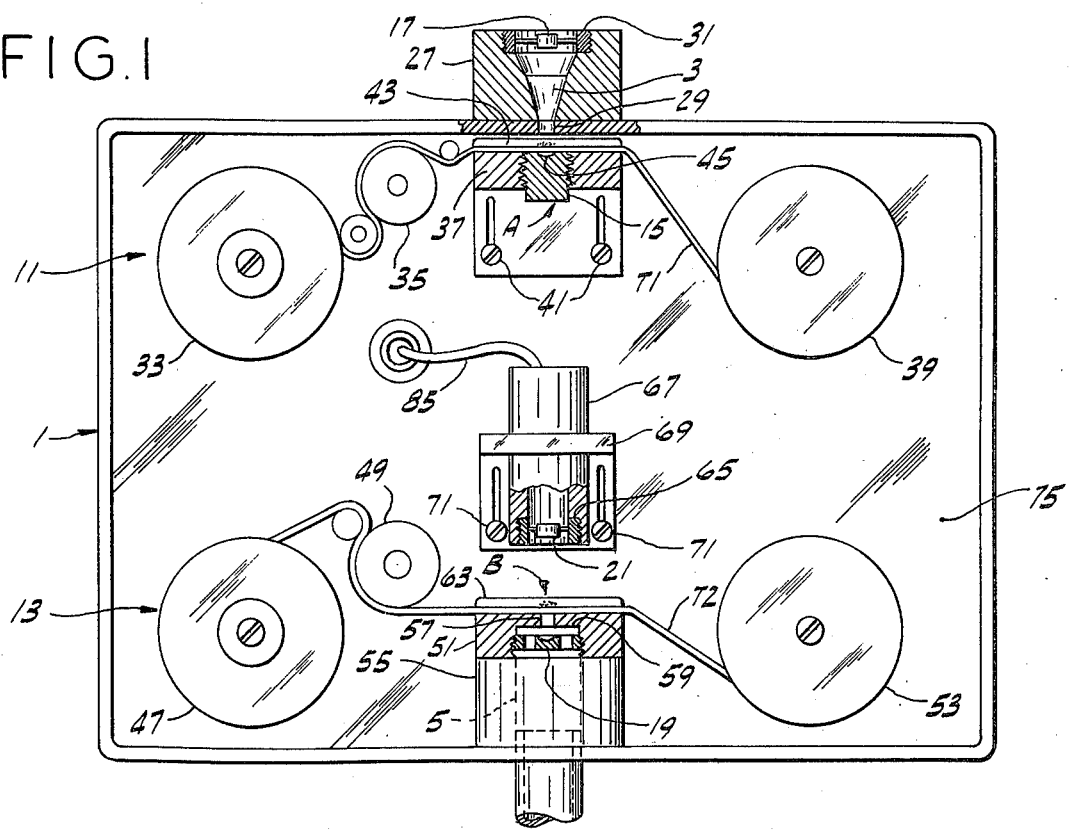

MONITOR FOR ATMOSPHERIC POLLUTANTS

BACKGROUND OF THE INVENTION

This invention relates to the monitoring of atmospheric pollutants and more particularly to the monitoring of the mass concentration of such pollutants above and below a given size.

Air borne particulates, or atmospheric pollutants, are of continuing concern because of their effects on human health, climatic conditions and visibility in many urban areas. Present air quality standards for these pollutants are expressed in terms of total aerosol mass. However, such a single parameter measurment may be inadequate, if not misleading, because it has been found that the pollutants being monitored have two size ranges, which may be referred to as coarse and fine, and that the pollutants in one size range are produced by different sources and are associated with different effects than pollutants in the other size range. The coarse or larger pollutants are typically 5 microns or greater in size and are composed of solid mineral material, while the fine or smaller pollutants are less than 1 micron in size and are liquid droplets consisting of an aqueous solution of salts and organic matter. As a result, new standards may soon result, in which the determination of aerosol mass and composition will be a function of particle size.

Mass monitoring of two ranges of pollutant size cannot be adequately performed using present methods such as high volume filtering and gravimetric weighing because such methods are too slow, require manual operations and are incapable of continuous on-line operation. Further, measuring techniques employing geiger counters, scintillation detectors and gas flow proportional counters and the like are unsuitable because they do not have the high sensitivity or efficiency required to obtain accurate data in a short period of time. This latter requirement is important because it has been experimentally found that the mass concentration of pollutants in each size range varies considerably over relatively short periods of time and is markedly influenced by such factors as rain.

SUMMARY OF THE INVENTION

Among the objects of the invention may be noted the provision of apparatus for monitoring the mass concentration of atmospheric pollutants above and below a predetermined size; the provision of such apparatus which is fully automated and capable of continuous on-line operations; the provision of such apparatus which is highly sensitive and efficient in the detection of pollutants; the provision of such apparatus capable of performing accurate measurements in relatively short periods of time; and the provision of such apparatus which is highly reliable, compact in size, low in cost and easy to maintain.

Briefly, an apparatus of the invention for monitoring the mass concentration of atmospheric pollutants above and below a predetermined size comprises a receptacle having an air inlet and outlet. Means are provided for continuously drawing air through the inlet and thence through the receptacle and the outlet. A first collector means in the receptacle collects pollutants above the predetermined size. This first collector means is movable through a first station and collects pollutants above the predetermined size from the air entering the receptacle through the inlet on successive areas thereof. A second collector means in the receptacle collects pollutants below the predetermined size. This second collector means is movable through a second station and collects pollutants below the predetemined size from the air which has passed the first station on successive areas thereof. Means are provided for holding a first source of radiation for passage thereof through the area of the first collector means at the first station. Means are provided for detecting radiation from the first source passing through the area of the first collector means. Means are provided for holding a second source of radiation for passage thereof through the area of the second collector means at the second station. Means are provided for detecting radiation from the second source passing through the area of the second collector means. Means are provided for periodically operating the collector means to move the pollutant-bearing areas thereof away from the stations and to bring fresh areas for collection of pollutants into position at the stations, the collector means dwelling between successive operations thereof. Means responsive to the first and second detecting means indicate the mass concentration of pollutants above and below the predetermined size for each dwell period between the successive operations of the collector means.

Other objects and features will be in part apparent and in part pointed out hereinafter.

BRIEF DESCRIPTION OF THE DRAWINGS

FIG. 1 is a front elevation of a receptacle of the apparatus of the invention with its lid removed and with certain portions shown in section; and FIG. 2 is a block diagram illustrating the major components of the apparatus of the invention and their interconnections.

Corresponding reference characters indicate corresponding parts throughout the several views of the drawings.

DESCRIPTION OF THE PREFERRED EMBODIMENT

Referring to the drawings, apparatus of this invention for monitoring the mass concentration of atmospheric pollutants above and below a predetermined size is shown to comprise a receptacle 1 having an air inlet 3, an air outlet 5, and means constituted by an air pump 7 having its inlet 9 connected to the outlet 5 of the receptacle for continuously drawing air through the inlet 3 and thence through the receptacle 1 and the outlet 5. At 11 is generally indicated a first collector means in the receptacle for collecting pollutants, consisting of airborne particulates, above a predetermined size (e.g., above 3 microns). This first collector means comprises a first tape T1 movable through a first station A at the inlet adapted to collect on successive areas thereof pollutants which are above said predetermined size from the air entering the receptacle through the inlet 3. At 13 is generally indicated a second collector means in the receptacle for collecting pollutants, also consisting of airborne particulates, below said predetermined size (e.g., below 3 microns). This second collector means comprises a second tape T2 movable through a second station B at the outlet adapted to collect on successive areas thereof pollutants which are below said predetermined size from the air which has passed the first station (and already had the larger pollutants removed by the tape T1).

At 15 is indicated means for holding a first source of radiation, preferably a beta radiation source, for passage thereof through the area of the first collector means 11, i.e., through the area of the first tape T1, at the first station A. At 17 is indicated means for detecting radiation passing through said area of the first tape. At 19 is indicated means for holding a second source of radiation, again preferably a source of beta radiation, for passage thereof through the area of the second collector means 13, i.e., through said area of the second tape T2, at the second station B. At 21 is indicated means for detecting radiation passing through said area of the second collector means. The first and the second collector means 11 and 13 are periodically operated by means indicated generally at 23 to move the pollutant-bearing areas thereof away from stations A and B and to bring fresh areas for collection of pollutants into position at said stations, both of the collector means dwelling at rest between successive operations thereof. Means indicated generally at 25 is provided operable in response to the first and second detecting means 17 and 21 for indicating the mass concentration of pollutants above and below the said predetermined size (e.g., above and below 3 microns) for each of the dwell periods between the successive operations of the two collector means.

The receptacle 1 may take the form of a portable carrying case having a handle and a lid adapted to be opened for access to the collecting means 11 and 13 and to be closed in relatively air-tight manner. On top of the receptacle is a cylindric block 27 in which the air inlet 3 is formed; the inlet including a relatively small opening 29 in the top of the case. The first detector 17 is carried by a spider 31 secured in the inlet, the spider permitting flow of air past the detector through the inlet.

The first collector means 11 comprises a tape transport including a spool 33 for holding a supply of the first tape T1, and a metering roll 35 for drawing a metered length of tape from the spool 33 and feeding it forward over a tape guide 37 to a take-up spool 39. The tape passes over the top of the guide in close proximity to but spaced from the top of the receptacle. The guide is vertically adjustable as indicated at 41 and has side flanges such as indicated at 43 for guiding the tape. Air entering the receptacle through the opening 29 in the top of the receptacle strikes an area of the upper surface of the tape T1 at station A, and then flows down into the receptacle below the guide, as permitted by the spacing of the guide from the top of the case. The tape T1 is adapted to collect pollutants above a predetermined size (e.g., above 3 microns) from the air striking said area of the tape over said area, which corresponds generally to the area of the opening 29. For this purpose, the tape T1 may be a cellulose-backed, glass-fiber tape such as that commercially available from Pallflex Products Corporation under its model designation E70, which is of high efficiency in collecting pollutants. The means 15 for holding the first source of radiation comprises a plug threaded in a tapped hole in the guide, this plug having a cavity 45 in the top for holding a source of beta radiation, such as carbon 14 ($14_c$) or other suitable material. The carbon 14 is deposited in cavity 45 in a suitable form, for example, as barium carbonate (BaCO3) which is mixed with a suitable adhesive. Cavity 45 is covered with a thin film (not shown).

The second collector means 13 comprises a tape transport including a spool 47 for holding a supply of the second tape T2, and a metering roll 49 for drawing a metered length of tape from the spool 47 and feeding it forward over a tape guide 51 to a take-up spool 53. The guide 51 is mounted on top of a cylindric block 55 which extends up from the bottom of the receptacle, the air outlet 5 being formed in this block. The guide 51 has a relatively small central opening 57 constituting the entrance to the outlet, with a tapped counterbore 59 in which is threaded a spider constituting the means 19 for holding the second source of radiation (which may also be a source of carbon 14 deposited in a similar manner to that in cavity 45). The tape passes over the top of the guide 51, which has side flanges such as indicated at 63 for guiding the tape. Air in the receptacle which has passed station A is drawn through the area of the tape T2 at the opening 57 and flows down and exits from the receptacle via the outlet 5. The tape T2 is a filter tape adapted to collect pollutants below said predetermined size (remaining in the air after the air has passed station A) over said area of the tape corresponding to the area of opening 57. For this purpose, the tape T2 may also be a cellulose-backed, glass-fiber tape of high efficiency in collecting pollutants. The second detector 21 is carried by a spider 65 in the lower end of a holder 67 carried by a bracket 69 which is vertically adjustable as indicated at 71 toward and away from the top of the guide 51. Air flow is around holder 67 and bracket 69 to strike and pass through the tape T2 into the opening 57.

The collector means 11 and 13 are located on one side of a partition 75 in the receptacle 1. The means 23 for periodically operating the collector means 11 and 13, which may be located in the receptacle on the other side of this partition, comprises an electric motor 77, suitable conventional drive means 79 from this motor to the take-up spools 39 and 53, a timer 81 for periodically energizing the motor (e.g., once every 30 minutes) to drive the take-up spools, and means 83 responsive to rotation of the metering rolls through a predetermined number of degrees for deenergizing the motor to effect feeding of a predetermined length of each tape corresponding to extent of metering roll rotation on each tape feed cycle.

Detectors 17 and 21 are solid-state, surface-barrier, beta radiation detectors such as are commercially available from ORTEC Incorporated of Oak Ridge, Tennessee, under their model designation R-016-050-100. Each detector is comprised of a silicon semiconductor chip with a Lithium surface deposit. A bias voltage is applied to each chip; this bias voltage and the output of each detector being commonly provided through a coaxial cable, such as cable 85 shown in FIG. 1. For purposes of drawing clarity, the connection of cable 85 to detector 21 is not shown in FIG. 1, nor is a connection shown between detector 17 and a coaxial cable which is represented by the line 87 in FIG. 2.

The means 25 responsive to the detecting means (detectors 17 and 21) includes preamplifiers 89 and 91, and amplifier/discriminators 93 and 95. These devices serve to amplify the response of each detector and discriminate between each detector's response and noise. Preamplifiers 89 and 91 are low-noise, charge-sensitive preamplifiers with very fast rise times, and are commercially available from ORTEC Incorporated of Oak Ridge, Tenn., under their model designation 125. Each preamplifier is sensitive to the change in charge which occurs when the respective detector 17 or 21 detects beta radiation to provide an electrical output signal. Amplifier/Discriminators 93 and 95, which are commercially available from Tennelec Incorporated under their model designation TC213, are low-noise gaussian-shaping amplifiers which serve to shape the output signals provided by the preamplifiers so that they may be utilized by conventional counting circuits.

The amplified responses of detectors 17 and 21 are counted by counters 97 and 99 respectively. These counters, which are commercially available from Tektronix Incorporated of Beaverton, Ore. under their model designation DC 503, count the detector responses for a period determined by a timer 101, this period being, for example, fifteen minutes. Thus, two counting cycles may occur between successive operations of first and second collector means 11 and 13.

At the end of each counting period, the contents of counters 97 and 99 are supplied to a calculator 103. Calculator 103, which is commercially available from Tektronix Incorporated of Beaverton, Ore. under its model designation 31/35, calculates the mass concentration of pollutants above and below the predetermined size (i.e., above and below 3 microns) as a function of the contents of counters 97 and 99 at end of the dwell period, the contents of counters 97 and 99 at the end of the prior dwell period, the transverse or cross-sectional area of the respective tapes used in collector means 17 and 19, and the flow rate of air through receptacle 1. The formula used in these calculations is $M = (A/f\lambda_m) \ln (I_o/I)$ where $M$ is the mass concentration of pollutants above or below the predetermined size, $A$ is the cross-sectional area of the tape, $f$ is the flow rate of air through receptacle 1, $\mu_m$ is a mass attenuation coefficient, $I_o$ is the contents of counter 97 or 99 at the end of the previous dwell period, and $I$ is the contents of counter 97 or 99 at the end of the present dwell period.

The mass concentration values calculated by calculator 103 are supplied to a conventional $x$-$y$ plotter 105 and a conventional printer 107. These means are responsive to calculator 103 to provide a visual indication of the mass concentration of the pollutants above and below the predetermined size (i.e., above and below 3 microns) either in the form of a pair of plotted paints on a graph or in the form of a digital printout. Further, the calculated mass concentration values are supplied to a tape recorder 109. Recorder 109 is responsive to calculator 103 to record the values of the mass concentrations of the pollutants above and below the predetermined size on a magnetic tape 111 for future use.

In operation, the tapes T1 and T2 are drawn from their respective supply spools 33 and 47, across their respective tape guides 37 and 51, to their respective take-up spools 39 and 53, all as shown in FIG. 1. Fresh collection areas of tapes T1 and T2 are thus present at the respective first and second stations A and B. At station A, beta radiation from the source in cavity 45 is emitted upward, through the collection area of tape T1 and opening 29 to beta radiation detector 17. At station B, beta radiation from the source in holder 19 is emitted upward through the opening 57 and the collection area of tape T2 to beta radiation detector 21.

Pump 7 is continuously driven to continuously draw air through air inlet 3, opening 29, receptacle 1, and opening 57, to outlet 9, at a predetermined flow rate (e.g., approximately 12 liters of air per minute). The air contains pollutants whose sizes are both above and below the predetermined size (e.g., above and below 3 microns). When air is drawn through opening 29, the pollutants in the air, whose sizes are above the predetermined size, impact on the collection area of tape T1 at station A and remain on the tape. The air, with the remainder of the pollutants, is drawn through receptacle 1, toward opening 57. To reach opening 57, the air must pass through the collection area of tape T2, and in doing so, tape T2, acting as a filter, removes all the pollutants remaining in the air, i.e., those pollutants whose sizes are below the predetermined size.

Initially, all the beta radiation from the first and second sources reach the respective beta radiation detectors 17 and 21. As a result, the amount of radiation detected is very high and this is reflected by a high initial count rate at counters 97 and 99. As air continues to be drawn into and through receptacle 1, the amount of pollutants collected at stations A and B begins to increase. As this occurs, the beta radiation from the respective sources begins to interact with the pollutants accumulated at the collection areas of tapes T1 and T2 and the amount of radiation reaching detectors 17 and 21 begins to decrease. This is reflected in a decreasing count rate at counters 97 and 99. The more pollutants above or below the predetermined size there are in the air being drawn into receptacle 1, the greater will be the decrease in the amount of radiation being detected at station A or B.

After each stated counting period has elapsed timer 101 inhibits counters 97 and 99 from counting any additional responses of detectors 17 and 21 respectively. The contents of each counter is then provided to calculator 103 for use in performing the calculation of the respective mass concentrations. After the dwell period, timer 81, as previously discussed, energizes motor 77, which, via drive means 79, drives take-up spools 39 and 53 to move the pollutant-bearing areas of tapes T1 and T2 away from stations A and B and to move fresh areas of the tapes for the collection of pollutants into position at the two stations. When this operation is complete, a new dwell period begins.

In view of the above, it will be seen that the several objects of the invention are achieved and other advantageous results attained.

As various changes could be made in the above constructions without departing from the scope of the invention, it is intended that all matter contained in the above description shall be interpreted as illustrative and not in a limiting sense.

What is claimed is:

1. Apparatus for monitoring the mass concentrations of atmospheric pollutants above and below a predetermined size, comprising:
    a receptacle having an air inlet and outlet;
    means for continuously drawing air through the inlet and thence through the receptacle and the outlet;
    a first collector means in the receptacle for collecting pollutants above said predetermined size, said first collector means being movable through a first station and being adapted to collect pollutants above said size from the air entering the receptacle through the inlet on successive areas thereof;
    a second collector means in the receptacle for collecting pollutants below said predetermined size, said collector means being movable through a second station and being adapted to collect pollutants below said size from the air which has passed the first station on successive areas thereof;

means for holding a first source of radiation for passage thereof through said area of the first collector means at the first station;

means for detecting radiation from said first source passing through said area of the first collector means;

means for holding a second source of radiation for passage thereof through said area of the second collector means at the second station;

means for detecting radiation from said second source passing through said area of the second collector means;

means for periodically operating said collector means to move the pollutant-bearing areas thereof away from said stations and to bring fresh areas for collection of pollutants into position at said stations, the collector means dwelling between successive operations thereof; and means responsive to said first and second detecting means for indicating the mass concentration of pollutants above and below said predetermined size for each dwell period between the successive operations of the collector means.

2. Apparatus as set forth in claim 1 wherein each collector means comprises a tape transport, the tape of the first collector means being adapted to collect pollutants above said predetermined size and the tape of the second collector means being adapted to collect pollutants below said predetermined size.

3. Apparatus as set forth in claim 2 wherein said sources are beta radiation sources and said detecting means are beta radiation detectors.

4. Apparatus as set forth in claim 1 wherein said first holding means is located on the inside of the first tape and the first detector is located in the inlet on the outside of the tape, and the second holding means is located in the outlet on the outside of the second tape and the second detector is located on the inside of the second tape.

5. Apparatus as set forth in claim 4 wherein the means responsive to the detecting means includes means for amplifying the responses of each detector and for discriminating between each detector's responses and noise.

6. Apparatus as set forth in claim 5 further including means for counting the amplified responses of each detector for each dwell period between successive operations of the collector means.

7. Apparatus as set forth in claim 6 further including means for calculating the mass concentration of pollutants above and below the predetermined size as a function of the contents of the counting means at the end of each dwell period, the contents of the counting means at the end of the prior dwell period, the cross-sectional area of the respective tape, and the flow rate of air through the receptacle.

8. Apparatus as set forth in claim 7 further including means responsive to the calculation means to provide a visual indication of the mass concentration of the pollutants above and below the predetermined size.

9. Apparatus as set forth in claim 8 further including means responsive to the calculation means for recording the mass concentrations of the pollutants above and below the predetermined size on magnetic tape.

10. Apparatus as set forth in claim 1 wherein the means for periodically operating the first and second collector means comprises electric motor means for driving said collector means, and timer means for periodically energizing said motor means for an interval such as to move the pollutant-bearing areas of the collector means away from said stations and bring fresh areas for collection of pollutants into position at said stations.

11. Apparatus as set forth in claim 1 wherein the means for drawing air comprises an air pump having its inlet connected to the outlet of said receptacle.

12. The method of monitoring mass concentrations of atmospheric pollutants above and below a predetermined size, comprising:

causing air from the atmosphere to flow at a predetermined rate and for a predetermined period of time against an area of a first collector for collecting pollutants above said size and thence against an area of a second collector for collecting pollutants below said size;

directing radiation through said area of each collector; and detecting radiation passing through each area as a measure of the mass concentration of pollutants above and below said size for said period.

13. The method of claim 12 wherein said collectors are periodically moved to move the pollutant-bearing areas out of the flow of air and bring fresh areas into the flow of air.

14. The method of claim 13 wherein each collector is a tape and the two tapes are simultaneously periodically moved to move the pollutant-bearing area of each tape out of the flow of air and to bring a fresh area of each tape into the flow of air.

15. The method of claim 14 wherein said measure of mass concentration is determined by counting the amount of radiation which is detected during the predetermined period of time and by calculating the mass concentration of atmospheric pollutants above and below the predetermined size as a function of the amount of detected radiation counted during the predetermined period, the amount of detected radiation counted during the prior predetermined period, the cross-sectional areas of each tape, and the flow rate of the air.

* * * * *